(12) United States Patent
Mackenzie

(10) Patent No.: US 8,679,194 B2
(45) Date of Patent: Mar. 25, 2014

(54) EXPULSION LINER FOR PROSTHETIC OR ORTHOTIC DEVICES AND ASSOCIATED METHODS

(75) Inventor: Craig Mackenzie, Orlando, FL (US)

(73) Assignee: Evolution Industries, Inc., Orlando, FL (US)

( * ) Notice: Subject to any disclaimer, the term of this patent is extended or adjusted under 35 U.S.C. 154(b) by 6 days.

(21) Appl. No.: 12/657,454

(22) Filed: Jan. 21, 2010

(65) Prior Publication Data

US 2010/0185300 A1 Jul. 22, 2010

Related U.S. Application Data

(60) Provisional application No. 61/205,513, filed on Jan. 21, 2009.

(51) Int. Cl.
*A61F 2/80* (2006.01)

(52) U.S. Cl.
USPC ............................................................ 623/36

(58) Field of Classification Search
USPC ..................................................... 623/27–37
See application file for complete search history.

(56) References Cited

U.S. PATENT DOCUMENTS

| | | |
|---|---|---|
| 980,457 A | 1/1911 | Toles |
| 1,389,824 A | 11/1921 | Abrams |
| 1,893,853 A | 1/1933 | Tullis |
| 2,325,656 A | 8/1943 | Brophy |
| 2,530,285 A | 11/1950 | Catranis |
| 2,533,404 A | 12/1950 | Sharp et al. |
| 2,634,424 A | 4/1953 | O'Gorman et al. |
| 2,671,225 A | 3/1954 | Schoene et al. |
| 2,808,593 A | 10/1957 | Andersen |
| 3,393,407 A | 7/1968 | Andel |
| 3,587,572 A | 6/1971 | Evans |
| 3,671,980 A | 6/1972 | Baird ................................. 3/20 |
| 4,319,413 A | 3/1982 | Mattil |
| 4,474,573 A | 10/1984 | Detty |
| 4,885,828 A | 12/1989 | Kozlowski |
| 4,908,037 A | 3/1990 | Ross |
| 4,923,474 A | 5/1990 | Klasson et al. ................. 623/33 |

(Continued)

FOREIGN PATENT DOCUMENTS

| | | |
|---|---|---|
| DE | 745 981 | 5/1944 |
| DE | 813190 | 9/1951 |

(Continued)

OTHER PUBLICATIONS

Iceross® Confort® Locking/Cushion product information brochure, Mar. 27, 2009, 3 pages.

(Continued)

*Primary Examiner* — Bruce E Snow
(74) *Attorney, Agent, or Firm* — Workman Nydegger

(57) ABSTRACT

The expulsion liner is for use with a prosthetic device to be secured to a residual limb. The expulsion liner includes an elongated elastomeric tube having a closed distal end and an open proximal end, and defining an interior space configured to receive the residual limb. A one-way valve is positioned within the closed distal end and provides controlled fluid communication between the interior space and an external environment. The one-way valve may be configured to allow the weight of a user, via the residual limb, to expel moisture and air from the interior space out to the external environment.

15 Claims, 1 Drawing Sheet

(56) References Cited

U.S. PATENT DOCUMENTS

| | | | |
|---|---|---|---|
| 5,007,937 A | 4/1991 | Fishman et al. | 623/34 |
| 5,139,523 A | 8/1992 | Paton et al. | 623/37 |
| 5,163,965 A | 11/1992 | Rasmusson et al. | 623/36 |
| 5,226,918 A | 7/1993 | Silagy et al. | 623/32 |
| 5,244,716 A | 9/1993 | Thornton et al. | |
| 5,314,496 A | 5/1994 | Harris et al. | 623/31 |
| 5,376,129 A | 12/1994 | Raulkner et al. | 623/33 |
| 5,376,131 A | 12/1994 | Lenze et al. | 623/34 |
| 5,549,709 A | 8/1996 | Caspers | 623/26 |
| 5,593,454 A | 1/1997 | Helmy | |
| 5,658,353 A | 8/1997 | Layton | 623/34 |
| 5,702,489 A | 12/1997 | Slemker | 623/34 |
| 5,718,925 A | 2/1998 | Kristinsson et al. | 425/2 |
| 5,728,170 A | 3/1998 | Becker et al. | 623/37 |
| 5,735,906 A | 4/1998 | Caspers | 623/34 |
| 5,830,237 A | 11/1998 | Kania | |
| 5,885,674 A | 3/1999 | Maemoto et al. | |
| 5,888,216 A | 3/1999 | Haberman | 623/36 |
| 5,904,722 A | 5/1999 | Caspers | 623/34 |
| 5,931,872 A | 8/1999 | Lohmann | 623/36 |
| 5,972,036 A | 10/1999 | Kristinsson et al. | 623/33 |
| 5,980,577 A | 11/1999 | Radis et al. | |
| 6,076,284 A | 6/2000 | Terlizzi | |
| 6,136,039 A | 10/2000 | Kristinsson et al. | |
| 6,149,691 A | 11/2000 | Fay et al. | 623/37 |
| 6,171,431 B1 | 1/2001 | Gallagher, Jr. et al. | |
| 6,231,616 B1 | 5/2001 | Helmy | 623/34 |
| 6,231,617 B1 | 5/2001 | Fay | 623/36 |
| 6,273,918 B1 | 8/2001 | Yuhasz et al. | 623/33 |
| 6,287,345 B1 | 9/2001 | Slemker et al. | 623/34 |
| 6,361,568 B1 * | 3/2002 | Hoerner | 623/32 |
| 6,406,499 B1 | 6/2002 | Kania | |
| 6,485,776 B2 | 11/2002 | Janusson et al. | |
| 6,508,842 B1 | 1/2003 | Caspers | 623/32 |
| 6,544,292 B1 * | 4/2003 | Laghi | 623/36 |
| 6,554,868 B1 | 4/2003 | Caspers | 623/34 |
| 6,585,774 B2 | 7/2003 | Dean, Jr. et al. | 623/37 |
| 6,626,952 B2 | 9/2003 | Janusson et al. | |
| 6,645,253 B2 | 11/2003 | Caspers | 623/26 |
| 6,706,364 B2 | 3/2004 | Janusson et al. | |
| 6,726,726 B2 | 4/2004 | Caspers | 623/34 |
| 6,761,742 B2 | 7/2004 | Caspers | 623/34 |
| 6,852,269 B2 | 2/2005 | Eberle et al. | |
| 6,964,688 B1 | 11/2005 | Kania | |
| 7,001,563 B2 | 2/2006 | Janusson et al. | |
| 7,025,793 B2 | 4/2006 | Egilsson | |
| 7,118,602 B2 | 10/2006 | Bjarnason | |
| 7,169,189 B2 | 1/2007 | Bjarnason et al. | |
| 7,235,108 B2 | 6/2007 | Carstens | |
| 7,291,182 B1 | 11/2007 | Kania | |
| 7,351,264 B2 | 4/2008 | Wilson | |
| 7,427,297 B2 | 9/2008 | Patterson et al. | |
| 7,749,281 B2 | 7/2010 | Egilsson | |
| 7,771,487 B2 | 8/2010 | Mantelmacher | |
| 8,034,120 B2 | 10/2011 | Egilsson et al. | |
| 2001/0005798 A1 | 6/2001 | Caspers | 623/34 |
| 2001/0016781 A1 | 8/2001 | Caspers | 623/34 |
| 2002/0040248 A1 | 4/2002 | Karason | 623/37 |
| 2002/0087215 A1 | 7/2002 | Caspers | 623/34 |
| 2002/0091449 A1 | 7/2002 | Caspers et al. | 623/34 |
| 2002/0099450 A1 | 7/2002 | Dean, Jr. et al. | 623/26 |
| 2002/0165619 A1 | 11/2002 | Hellberg | |
| 2002/0183859 A1 | 12/2002 | Houser | |
| 2003/0181989 A1 | 9/2003 | Eberle et al. | |
| 2003/0191539 A1 | 10/2003 | Caspers | 623/35 |
| 2004/0030411 A1 | 2/2004 | Caspers | 623/37 |
| 2004/0098136 A1 | 5/2004 | Caspers | 623/34 |
| 2004/0122528 A1 | 6/2004 | Egilsson | 623/34 |
| 2004/0143345 A1 | 7/2004 | Caspers | 623/36 |
| 2004/0167638 A1 | 8/2004 | Caspers | 623/27 |
| 2004/0181290 A1 | 9/2004 | Caspers | 623/34 |
| 2004/0236434 A1 | 11/2004 | Carstens | 623/34 |
| 2004/0243251 A1 | 12/2004 | Carstens | 623/34 |
| 2004/0243252 A1 | 12/2004 | Carstens | 623/34 |
| 2005/0240282 A1 | 10/2005 | Rush et al. | |
| 2005/0240283 A1 | 10/2005 | Kania | |
| 2007/0027556 A1 | 2/2007 | Wilson | |
| 2007/0043450 A1 | 2/2007 | Pickering et al. | |
| 2007/0055383 A1 * | 3/2007 | King | 623/34 |
| 2007/0061017 A1 | 3/2007 | Wilson | |
| 2007/0123998 A1 | 5/2007 | Egilsson et al. | |
| 2007/0179606 A1 | 8/2007 | Huyghe et al. | |
| 2008/0147202 A1 | 6/2008 | Danzig et al. | |
| 2008/0188949 A1 | 8/2008 | MacKenzie | |
| 2008/0221705 A1 | 9/2008 | Scussel | |
| 2008/0221706 A1 | 9/2008 | Scussel et al. | |
| 2008/0269914 A1 | 10/2008 | Coppens et al. | |
| 2009/0036999 A1 | 2/2009 | Egilsson et al. | |
| 2009/0157196 A1 | 6/2009 | Danzig et al. | |
| 2009/0198346 A1 | 8/2009 | Perkins et al. | |
| 2009/0240344 A1 | 9/2009 | Colvin et al. | |
| 2009/0306791 A1 | 12/2009 | Slemker et al. | |
| 2010/0070051 A1 | 3/2010 | Carstens | |
| 2010/0185300 A1 | 7/2010 | Mackenzie | |
| 2010/0274364 A1 | 10/2010 | Pacanowsky et al. | |
| 2010/0318196 A1 | 12/2010 | Egilsson | |
| 2011/0029096 A1 | 2/2011 | Laghi | |
| 2011/0035027 A1 | 2/2011 | McCarthy | |
| 2011/0071649 A1 | 3/2011 | McKinney | |
| 2011/0077748 A1 | 3/2011 | Egilsson et al. | |
| 2011/0118854 A1 | 5/2011 | Halldorsson | |

FOREIGN PATENT DOCUMENTS

| | | |
|---|---|---|
| DE | 1795809 | 9/1959 |
| DE | 2060239 | 6/1972 |
| DE | 2540138 | 3/1977 |
| DE | 3221920 | 4/1983 |
| DE | 3508919 | 11/1989 |
| DE | 9419208 | 11/1994 |
| EP | 0 631 765 | 9/1998 |
| FR | 2 828 093 A1 | 8/2001 |
| GB | 267988 | 9/1925 |
| GB | 2069847 | 9/1981 |
| GB | 2087727 | 6/1982 |
| JP | 07155343 | 6/1995 |
| WO | WO 97/34548 | 9/1997 |
| WO | 00/74611 | 12/2000 |
| WO | 01/54631 | 8/2001 |
| WO | 01/67842 A1 | 9/2001 |
| WO | WO 02/26158 | 4/2002 |
| WO | 03/024367 | 3/2003 |
| WO | 03/024370 | 3/2003 |
| WO | 03/039398 | 5/2003 |
| WO | 03/099173 | 12/2003 |

OTHER PUBLICATIONS

Iceross® Dermo, product information sheets from Internet, http://www.ossur.com/prosthetics/liners/dermo, Mar. 27, 2009, 2 sheets.

Military inStep: Prosthetic Socks and Liners, product information sheets from Internet, http//www.amputee-coalition.org/military-in-step/prosthetic-socks, Mar. 27, 2009, 3 pages.

Prosthetic & Orthotic Update NewsLetter, No. 32, Internet Search conducted Mar. 27, 2009, 4 pages.

Walopur® Platilon@U, Product Information Brochure of Epurex Films GmbH & Co., KG, Internet Search result conducted Maarch 27, 2009, 2 pages.

EP 03 78 9861—Supplementary European Search Report.

* cited by examiner

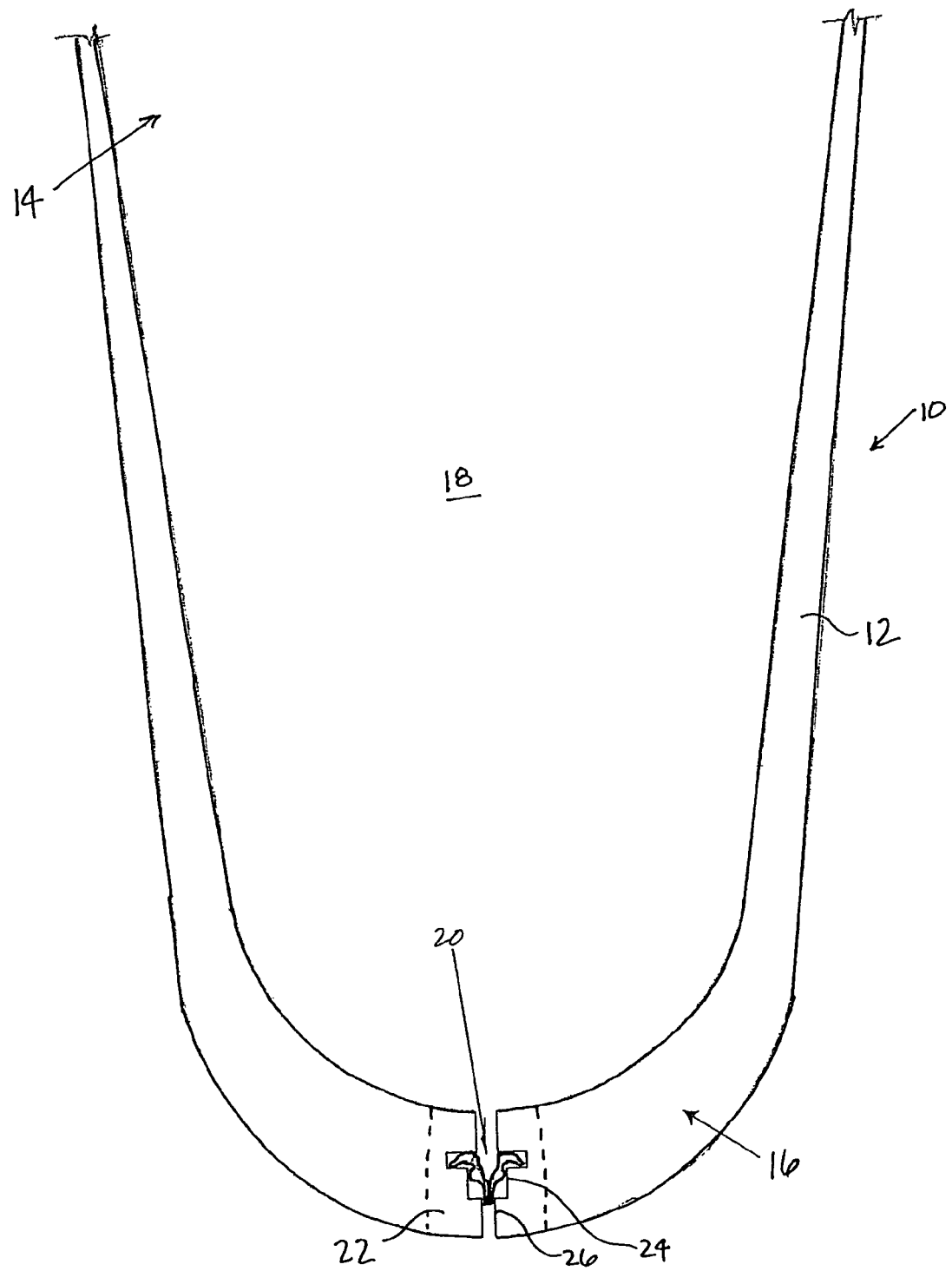

EXPULSION LINER FOR PROSTHETIC OR ORTHOTIC DEVICES AND ASSOCIATED METHODS

RELATED APPLICATION

This application claims priority to a copending provisional application Ser. No. 61/205,513 filed Jan. 21, 2009, the entire disclosure of which is incorporated herein by reference.

FIELD OF THE INVENTION

The present invention relates to the field of prosthetic and orthotic liners (i.e. skin-socket interface liners), and more particularly to custom and production ("off the shelf") prosthetic liners and associated methods.

BACKGROUND OF THE INVENTION

Liners provide a soft, flexible interface between a residual limb of an amputee and a hard socket to which a prosthetic device is secured. Such liners are typically made of an elastomer material such as silicone. Such liners may also be used in connection with orthotic devices. Prosthetic suspension liners are described in prior patents, and may be fabricated of elastomer or rubber materials, and are used to cushion a post-operative stump or residual limb with respect to a prosthesis that is installed over the residual limb and coupled to the liner, e.g. by a conventional locking device.

Such liners should conform closely with the residual limb, accommodate all surface contours and sub-surface bone elements of the residual limb, and provide a comfortable cushion between the residual limb and the hard socket of the prosthesis that is to be fitted over the residual limb. Various silicone rubber or elastomer materials are used for suspension liners. Such elastomer materials having an appropriate hardness/softness, elongation, tensile, and other properties, such as bio-inertness (resulting in no skin reaction), have been successfully used for suspension liners.

The elastomer forming the liner frictionally engages and remains attached to the skin of a residual limb so that the limb is retained within the prosthetic socket in a comfortable, non-irritating manner. For example, liners may be used for any level of amputation both upper and lower limb. Prosthetic liners are used to cushion the amputee's residual limb from shock during ambulation.

Amputee limb heath is an important factor in prosthetic liner choice. During normal ambulation the residual limb can produce perspiration that accumulates in the distal end of the liner. With the advent of vacuum assisted or suction socket systems the residual limb is surrounded in a non-permeable material that may trap perspiration or air against the skin, this environment may be detrimental to limb health.

Another consequence of moisture or air against the residual limb is the possibility of losing the link between the liner and skin. A loss of linkage could result in the detachment or loss of the prosthesis.

SUMMARY OF THE INVENTION

It is an object of the present invention to provide a more reliable liner for a prosthetic device that reduces trapped moisture around the skin.

This and other objects, advantages and features in accordance with the present invention are provided by an expulsion liner for use with a prosthetic device to be secured to a residual limb. The expulsion liner includes an elongated elastomeric tube having a closed distal end and an open proximal end, and defining an interior space configured to receive the residual limb. A one-way valve is positioned within the closed distal end and provides controlled fluid communication between the interior space and an external environment.

The one-way valve may be configured to allow the weight of a user, via the residual limb, to expel moisture and air from the interior space out to the external environment. The one-way valve may be a duckbill valve and/or have a cracking pressure of about 0.2 psi. The distal end of the elongated elastomeric tube may include a reinforcing feature adjacent the one-way valve to secure a positioning thereof.

Objects, advantages and features in accordance with the present invention are also provided by a method of making an expulsion liner for use with a prosthetic device to be secured to a residual limb. The method includes forming an elongated elastomeric tube having a closed distal end and an open proximal end, and defining an interior space configured to receive the residual limb, and positioning a one-way valve within the closed distal end and providing controlled fluid communication between the interior space and an external environment.

BRIEF DESCRIPTION OF THE DRAWING

FIG. 1 is a cross-sectional view of a liner including a main body and a one-way valve integrated at a distal end thereof.

DETAILED DESCRIPTION OF THE PREFERRED EMBODIMENTS

The present invention will now be described more fully hereinafter with reference to the accompanying drawings in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The dimensions of layers and regions may be exaggerated in the figures for ease of explanation.

The following description refers to, by example, a liner associated with the knee, however, the features of the invention apply to liners for use with any limb/joint area that may benefit from the use of a distal valve as described herein. Features of the present invention are directed to a prosthetic liner and associated methods of making and using, and includes the use of an elastomer material, e.g. pourable or injectable silicone, that may be used with a simple mold or press. The silicone is preferably biocompatible, e.g. "healthcare grade" or "medical grade", which is suitable for external use. For example, an appropriate silicone system may also be clear to semi-translucent and curable at room temperature. The molded silicone liner should have high tear strength and exhibit flexibility and high elasticity. Other elastomers or materials exhibiting the necessary qualities of a skin-interface liner may also be used.

Referring to FIG. 1, the approach of the present invention will be described. The expulsion liner 10 includes an elongated tube 12 of elastomer material having an open proximal end 14 and a closed distal end 16. The liner is donned by an amputee with the closed end 16 adjacent and preferably in close contact with a distal end of the residual limb. A one-way valve 20 is centrally positioned in the bottom, or distal end 16, of the liner 10. The weight of the amputee during ambulation will create enough force to push or expel perspiration or air out through the one-way valve 20 keeping the residual limb dry and creating a better environment for the residual limb. The one-way valve 20 should not allow air, moisture or any other contaminate to enter the interior space 18 of the liner 10.

A type of one-way valve 20 is a duckbill valve which is made of rubber and has a low cracking pressure, about 0.2 psi. Other types of one-way valves are also available and may be used in the expulsion liner 10.

The one-way valve may be seated in a mold prior to injecting the elastomer for the liner 10. An adapter may hold the one-way valve 20 in the mold and then may be removed before or after curing of the liner is complete. The liner 10 may also include a stiffening or reinforcing feature 22, such as a localized increased liner durometer, adjacent the one-way valve 20 to ensure the reliability of the expulsion liner.

Alternatively, the one-way valve 20 may be integrated with the liner 10 via a mechanical process after curing thereof. Such a process may include creating a chamber 24, and corresponding channel 26, or attachment area in the distal end of the liner 10, and then inserting or otherwise adhering the one-way valve 20 at the attachment area of the liner.

Thus, an expulsion liner 10 is provided for use with a prosthetic device to be secured to a residual limb. The expulsion liner 10 includes an elongated elastomeric tube 12 having a closed distal end 16 and an open proximal end 14, and defining an interior space 18 configured to receive the residual limb. A one-way valve 20 is positioned within the closed distal end 16 and provides controlled fluid communication between the interior space 18 and an external environment. Moisture, such as perspiration, and/or air, is expelled out through the one-way valve 20.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. An expulsion liner for use with a prosthetic device to be secured to a residual limb, the expulsion liner comprising:
   an elongated elastomeric tube formed of an elastomeric material having a closed distal end and an open proximal end, and defining an interior space configured to receive the residual limb, the closed distal end including a reinforcing feature comprising a localized increased stiffness area of the elastomeric material defined by a distal end thickness of the tube, the distal end thickness defining a channel extending through an entirety of the thickness between the interior space and an external environment; and
   a one-way valve positioned solely within the thickness of the localized increased stiffness area in the elastomeric material of the closed distal end and providing controlled fluid communication between the interior space and the external environment, a portion of the channel extending between the one-way valve and an outer periphery of the tube;
   wherein the one-way valve is centrally located at the bottom of the distal end of the liner.

2. The expulsion liner according to claim 1 wherein the one-way valve is configured to allow the weight of a user, via the residual limb, to expel moisture and air from the interior space out to the external environment.

3. The expulsion liner according to claim 1 wherein the one-way valve comprises a duckbill valve.

4. The expulsion liner according to claim 1 wherein the one-way valve has a cracking pressure of about 0.2 psi.

5. An expulsion liner for use with a prosthetic device to be secured to a residual limb, the expulsion liner comprising:
   an elongated elastomeric tube formed of an elastomeric material having a closed distal end and an open proximal end, and defining an interior space configured to receive the residual limb. the closed distal end including a reinforcing feature comprising a localized increased stiffness area of the elastomeric material defined by a distal end thickness of the tube, the distal end thickness defining a channel extending through an entirety of the thickness between the interior space and an external environment; and
   a duckbill valve solely positioned within the thickness of the localized increased stiffness area in the elastomeric material of the closed distal end configured to allow the weight of a user, via the residual limb, to expel moisture and air from the interior space out to the external environment, a portion of the channel extending between the one-way valve and an outer periphery of the tube;
   wherein the duckbill valve is centrally located at the bottom of the distal end of the liner.

6. The expulsion liner according to claim 5 wherein the duckbill valve has a cracking pressure of about 0.2 psi.

7. A method of making an expulsion liner for use with a prosthetic device to be secured to a residual limb, the method comprising:
   forming an elongated elastomeric tube formed of an elastomeric material having a closed distal end and an open proximal end, and defining an interior space configured to receive the residual limb, the closed distal end including a reinforcing feature comprising a localized increased stiffness area of the elastomeric material, defined by a distal end thickness of the tube;
   forming a channel extending through an entirety of the distal end thickness of the tube between an inner periphery to an outer periphery open at an external environment; and
   positioning a one-way valve solely within the localized increased stiffness area in the elastomeric material of the closed distal end and providing controlled fluid communication between the interior space and the external environment;
   wherein the one-way valve is centrally located at the bottom of the distal end of the liner;
   wherein a portion of the channel extends between the one-way valve and the outer periphery of the tube.

8. The method according to claim 7 wherein the one-way valve is configured to allow the weight of a user, via the residual limb, to expel moisture and air from the interior space out to the external environment.

9. The method according to claim 7 wherein the one-way valve comprises a duckbill valve.

10. The method according to claim 7 wherein the one-way valve has a cracking pressure of about 0.2 psi.

11. The expulsion liner according to claim 1, wherein another portion of the channel extends between an inner periphery of the tube at the distal end to the one-way valve.

12. The expulsion liner according to claim 1, wherein a thickness of the one-way valve is less than the distal end thickness.

13. The expulsion liner according to claim 1, wherein the one-way valve is embedded within the distal end thickness and spaced away by a clearance from the outer periphery of the tube.

14. The expulsion liner according to claim 1, wherein distal end thickness defines a chamber into which the one-way valve extends, the channel communicating the chamber to the outer periphery of the liner.

15. The expulsion liner according to claim 1, wherein the distal end thickness defines a maximum thickness of the tube.

\* \* \* \* \*